US006393760B1

(12) United States Patent
Lingren (10) Patent No.: US 6,393,760 B1
(45) Date of Patent: *May 28, 2002

(54) KAIROMONE AND KILL-BAIT CONTAINING INSECT TRAP

(75) Inventor: Bill W. Lingren, Carmel Valley, CA (US)

(73) Assignee: Trece, Inc., Salinas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/482,155

(22) Filed: Jan. 12, 2000

Related U.S. Application Data

(63) Continuation-in-part of application No. 09/047,191, filed on Mar. 19, 1998, now Pat. No. 6,018,905.
(60) Provisional application No. 60/041,305, filed on Mar. 19, 1997.

(51) Int. Cl.[7] ................................................ A01M 1/10
(52) U.S. Cl. ........................................... 43/122; 43/107
(58) Field of Search ........................... 43/107, 108, 121, 43/122

(56) References Cited

U.S. PATENT DOCUMENTS

| | | |
|---|---|---|
| 1,312,573 A | 8/1919 | Pichot |
| 1,772,989 A | 8/1930 | Emley |
| 2,715,295 A | 8/1955 | Brown .......................... 43/107 |
| 2,809,465 A | 10/1957 | Guinotte ....................... 43/122 |
| 4,121,372 A | 10/1978 | Landaus ........................ 43/122 |
| 4,198,782 A | 4/1980 | Kydonieus et al. ............. 47/58 |
| 4,244,135 A | 1/1981 | Harwoods ..................... 43/122 |
| 4,400,903 A * | 8/1983 | Seidenberger ................ 43/122 |
| 4,481,216 A | 11/1984 | Hubbard et al. ............. 424/300 |
| 4,657,926 A | 4/1987 | Pickett et al. ................ 514/467 |
| 4,718,193 A | 1/1988 | Rosselli ........................ 43/122 |
| 4,780,479 A | 10/1988 | Pickett et al. ................ 514/467 |
| 4,794,724 A | 1/1989 | Peters .......................... 43/122 |
| 4,851,218 A | 7/1989 | Hildebrandt et al. ........... 424/84 |
| 4,880,624 A | 11/1989 | Metcalf et al. ................ 424/84 |
| 4,885,177 A | 12/1989 | Wegmann ..................... 424/95 |
| 4,908,388 A | 3/1990 | Pickett et al. ................ 514/716 |
| 4,930,251 A | 6/1990 | Crisanti ........................ 43/107 |
| 4,981,981 A | 1/1991 | Aldrich et al. ............... 549/546 |
| 4,983,390 A | 1/1991 | Levy ........................... 424/404 |
| 5,057,316 A | 10/1991 | Gunner et al. ................. 424/93 |
| 5,133,150 A | 7/1992 | Briese .......................... 43/122 |
| 5,141,744 A | 8/1992 | Chang et al. .................. 424/93 |
| 5,167,955 A | 12/1992 | Teale et al. .................... 424/84 |
| 5,231,791 A | 8/1993 | Falkson ........................ 43/122 |
| 5,231,792 A | 8/1993 | Warner ......................... 43/122 |
| 5,392,560 A | 2/1995 | Donahue et al. .............. 43/122 |
| 5,396,729 A * | 3/1995 | Vejvoda ........................ 43/114 |
| 5,406,743 A | 4/1995 | McSherry et al. ............. 43/122 |
| 5,407,454 A | 4/1995 | Cavalieri et al. ............... 47/58 |
| 5,464,618 A | 11/1995 | Doane et al. ............. 424/195.1 |
| 5,522,171 A | 6/1996 | Mandeville ................... 43/122 |
| 5,558,862 A | 9/1996 | Corbin et al. ............... 424/94.4 |
| 5,571,522 A | 11/1996 | Munson et al. .............. 424/410 |
| 5,596,833 A | 1/1997 | Harrie et al. .................. 43/122 |
| 5,632,987 A | 5/1997 | Payne et al. ........... 424/93.461 |
| 5,682,706 A | 11/1997 | Altenburg ..................... 43/122 |
| 5,750,129 A | 5/1998 | Wakarchuk .................. 424/408 |
| 5,759,561 A | 6/1998 | Angst et al. ................. 424/407 |
| 5,842,305 A | 12/1998 | Liao ............................ 43/122 |

* cited by examiner

Primary Examiner—Kurt Rowan
(74) Attorney, Agent, or Firm—Hana Verny (57) ABSTRACT

An insect trap for capturing flying insects. The trap comprises a capture top dome, a capture reservoir, a kairomone lure dispenser and kill-bait. The method for capturing, killing and monitoring flying insect. The trap is useful for corn, peanuts and leafy vegetable crop protection from corn rootworm or other insects.

11 Claims, 5 Drawing Sheets

KAIROMONE AND KILL-BAIT CONTAINING INSECT TRAP

This application is a Continuation-in-part of application Ser. No. 09/047,191, filed on Mar. 19, 1998, now U.S. Pat. No. 6,018,905 issued on Feb. 1, 2000, which is based on the provisional application Ser. No.: 60/041,305 filed on Mar. 19, 1997.

BACKGROUND OF THE INVENTION

1. Field of the Invention

This invention concerns a generally useful kairomone and kill-bait containing insect trap for capturing insect in general and corn rootworm and other related insects feeding of and destroying Diabrotica, corn, peanut and leafy vegetable crops in particular. The trap comprises four major components: a top dome, a capture reservoir and a kairomone lure container attached externally to the top dome and an internally placed kill-bait. The trap additionally comprises means for attachment or emplacement of the trap in the field. The trap is useful for monitoring the infestation of the field and for killing the insect.

2. Background of the Invention

Flying insect in general and corn rootworm in particular poses a serious economic problem for Diabrotica, corn, peanuts and leafy vegetable crops.

Twenty-one million acres of corn are treated annually in many mid-western states with soil-applied preventative insecticides for controlling Western and/or Northern corn rootworm. Thousands of additional acres of corn, peanuts and leafy vegetables are attacked by two other rootworm species, the Southern and Mexican rootworm and also require similar treatments. United States Department of Agriculture (USDA) estimates that only about 30% of these treatments with insecticides are justified from an economic loss point of view. Moreover, for a variety of reasons, only a small portion of these treatments is successful because of the poor administration of the insecticide or because of the resistance the insect has developed toward the insecticide.

Monitoring of the infestation prior to the treatment with insecticides is difficult as there are currently no available suitable and practical monitoring devices.

Iowa State University and the USDA have correlated corn rootworm adult capture rates from PHEROCON® AM/NB yellow glue coated cards to counts of adults found on plants and these numbers have been then correlated to larval root pruning damage in corn. Currently, such monitoring is done almost solely by the PHEROCON® AM/NB yellow glue coated cards which, due mainly to inconvenience in their use, have been poorly received and were never adopted in any practical way.

Results of this correlation shows that the capture of corn rootworm using PHEROCON® AM/NB yellow glue coated cards is poor and, therefore, that some other methods of trapping, capture and monitoring of the corn rootworm and other similar insect are needed in order to reduce labor connected with field monitoring, time spent by consultants or pest control advisors on such monitoring and to predict, with high accuracy, the insect population and degree of infestation.

It would, therefore, be important and advantageous to have available a convenient and practical insect trap which would permit monitoring of flying insect, such as corn rootworm and related species, which would comprise specific means to attract and capture the insect and also monitor its number in order to determine whether additional treatment with insecticides is needed.

Many methods for prevention of insect infestation and crop destruction of corn, peanuts and leafy vegetables by corn rootworm or related insects were recently devised. Such methods for controlling corn rootworm include treatments with pathogens, the use of various chemicals and insect growth regulators, insect sex pheromones and other behavior modifying semiochemicals. Various insect traps have been devised which lure the insects, poison the insects, suffocate the insects and/or remove insects from the stored products using any of the above means.

The current invention provides a generally useful insect trap particularly suitable for capture of corn rootworm and other flying insect, said trap comprising several novel features making it extraordinarily practical and effective for capturing and monitoring the flying insect, particularly corn rootworm and other related insects feeding of and destroying corn, peanuts and leafy vegetable crops.

All patents, patent applications or publications cited herein are hereby incorporated by reference.

SUMMARY

One aspect of the current invention concerns a corn rootworm insect trap comprising a kairomone lure and/or kill-bait for capturing and killing the insect, particularly flying insect such as corn rootworm and other related insects which feed on and destroy Diabrotica, corn, peanuts and leafy vegetables.

Another aspect of the current invention is an insect trap which comprises a capture top dome, a capture reservoir, a container containing a kairomone to lure the insects to the trap and a kill-bait to kill the insects.

Still another aspect of the current invention is an insect trap suitable for capture of flying insect, said trap comprising of a top dome forming an upper portion of the trap containing in its upper center a kill-bait insertion slot for insertion of the kill-bait pill, said top dome further comprising locking and stop tabs of the locking device, and a capture reservoir forming a lower portion of the trap comprising a circumferential rim for locking the locking tabs of the top dome and effectively locking the capture reservoir to the top dome. Both the top dome and the capture reservoir are connected in such a fashion that the capture reservoir easily snaps into the top dome by engagement of the rim with the locking tabs of the top dome. Locking tabs, in cooperation with the stop tabs present on the top dome, control the size of the annular opening delineating the entryway for the insect into the trap. The trap additionally comprises of a separate kairomone lure component attached externally to the top dome. The kairomone lure is inserted into a female insertion slot positioned on the exterior surface of the top dome.

Still yet another aspect of the current invention are attachment means permitting the field stake to be inserted into a socket indented within the bottom of the capture reservoir and/or wire hanger to be inserted into attachment means extending upwardly as a protuberant top hanger from the center of the top dome.

Still yet another aspect of the current invention is a kill-bait pill for insertion within the kill-bait insertion slot positioned internally in the center upper part of the top dome, which kill-bait typically consists of a pill containing a mixture of cucurbitacin feeding stimuli with a carbaryl insecticide formulated in paraffin, such as in 60%, by volume, of paraffin of a melting point above 160° F.

Yet another aspect of the current invention is a kairomone lure holder which comprises a lure placed withing the lure holder sealed with a laminated seal consisting of an inner layer of plastic and an outer layer of foil.

Another aspect of the invention concerns the insect trap of the invention comprising solely a kill-bait without the kairomone lure.

Another aspect of the current invention is a method for capture of flying insect by means of the trap of the invention wherein the kairomone lure comprises an insect specific kairomone which lures the insect into the trap, for killing the insect with the kill-bait pill placed internally within the kill-bait insertion slot in the upper center of the top dome, and for monitoring the degree of infestation by counting the number of captured and killed insects present in the capture reservoir. The capture reservoir snaps into the top dome of the trap and can be easily opened, removed, emptied, exchanged or substituted for inspection or maintenance.

Yet another aspect of the current invention is a method for monitoring a number of insect infesting a crop field, said method comprising steps:

(a) luring the insect to the insect trap with an insect specific kairomone lure;

(b) luring the insects into the trap with kill-bait comprising cucurbitacin and an insecticide;

(c) capturing the dead insect in the capture reservoir; and (d) counting the number of captured and killed insect and expressing the number per day/week/month or any other selected period of time.

BRIEF DESCRIPTION OF DRAWINGS

FIG. 4 is a kairomone lure dispenser, front view (FIG. 4A), and side view (FIG. 4B).

DETAILED DESCRIPTION OF THE INVENTION

The current invention provides a novel insect trap for capture of insect generally and flying insect, such as corn rootworm (CRW), particularly.

The trap comprises essentially four main components: a capture top dome, a capture receptacle, a kairomone lure dispenser to lure the insects to the trap and a kill-bait which lures the insect into the trap by providing a feeding stimulant and kills the insect by the insecticide added to the feeding bait.

The invention, therefore, concerns an insect trap and methods for capturing and killing the insect and a method for monitoring the number of insects captured by one trap.

The trap comprises 1) a capture top dome, housing a kill-bait in its upper center; 2) a capture reservoir which is a receptacle or container collecting the captured and killed insect, which, in the assembled trap, is locked to the top dome in such a way as to provide insect with an easy access to the kill-bait; 3) a dispenser containing a kairomone lure to lure the insects to the trap which container is externally attached to the top dome; and 4) kill-bait pill to kill the insects lured within the internal space of the assembled trap wherein said kill-bait is placed in the kill-bait holder positioned in the upper center of the top dome. The top dome forms the upper portion of the assembled trap and the capture reservoir forms the lower portion of the trap wherein both the top dome and the reservoir are connected through locking device, namely, the locking tabs engaged with rim segments.

The locking device of the trap which permits locking the top dome and the reservoir components together comprises of the two or more, preferably three or four, locking tabs evenly circumferentially spaced withing the sloping down wall of the top dome as plastic protrusions or detents facing inwards and a circumferential continuous rim of the capture reservoir facing outwards, wherein said rim is interspaced with rim segments spaced to match the locking tabs. The locking tab detents of the top dome lock the rim segments of the reservoir only at sites where the tabs and segments are present, thereby leaving the space between the tabs open. Since the locking tabs and rim segments are evenly circumferentially spaced, these openings are also evenly distributed between the two adjacent locking tabs. For example, when there are three locking tabs, there are three openings in between the tabs. These openings form entryways through which the insect flies into the trap and toward the feeding stimulant present in the kill-bait pill.

The separate kairomone lure component of the trap is attached externally to the top dome. The kairomone lure component comprises of the kairomone lure, the lure holder and attachment means for attaching the holder to the top dome through insertion of a male insertion tab of the lure holder into a female insertion slot positioned on the exterior surface of the top dome. The lure in the kairomone lure holder is sealed with a laminated seal consisting of an inner layer of plastic and an outer layer of foil.

The trap additionally and optionally comprises one or more attachment means permitting either a field stake to be inserted into a socket positioned in the center of the capture reservoir bottom and/or wire hanger to be inserted into top hanger tap positioned in, and protruding externally from, the upper center of the top dome.

The trap is suitable for capture of flying insect which is lured toward the trap with the insect-specific kairomone and is further lured into the trap with the kill-bait. The kill-bait is typically a pill comprising a feeding stimulant in admixture with the killing agent. The kill-bait preferably consists of a pill containing a mixture of cucurbitacin feeding stimulant with a carbaryl insecticide bound together by a special formulation of paraffin, such as 60% paraffin by volume, of a melting point above 160° F.

The invention further concerns a method for 1) capture of flying insect by means of the trap of the invention as described above, wherein the kairomone lure comprises an insect specific kairomone which lures the insect into the trap, 2) killing the insect with the kill-bait placed inside of the top dome, and 3) monitoring the infestation by counting the number of captured and killed insects present in the capture reservoir which is removably attached to the top dome of the trap and can be easily opened, removed, emptied, exchanged or substituted for inspection or maintenance.

The method for capturing or killing the insect or monitoring a degree of infestation of crop fields comprises following steps:

(a) luring the insect to the insect trap with an insect specific kairomone lure;

(b) luring the insects into the trap with kill-bait comprising cucurbitacin or other feeding stimulant and an insecticide;

(c) capturing the dead insect in the capture receptacle; and (d) counting the number of captured and killed insect and expressing the kill number per day/week/month or any other selected period of time.

I. A Kairomone Containing Insect Trap

Kairomone containing insect trap and its four major components are shown in FIGS. 1–5.

Figure 1:
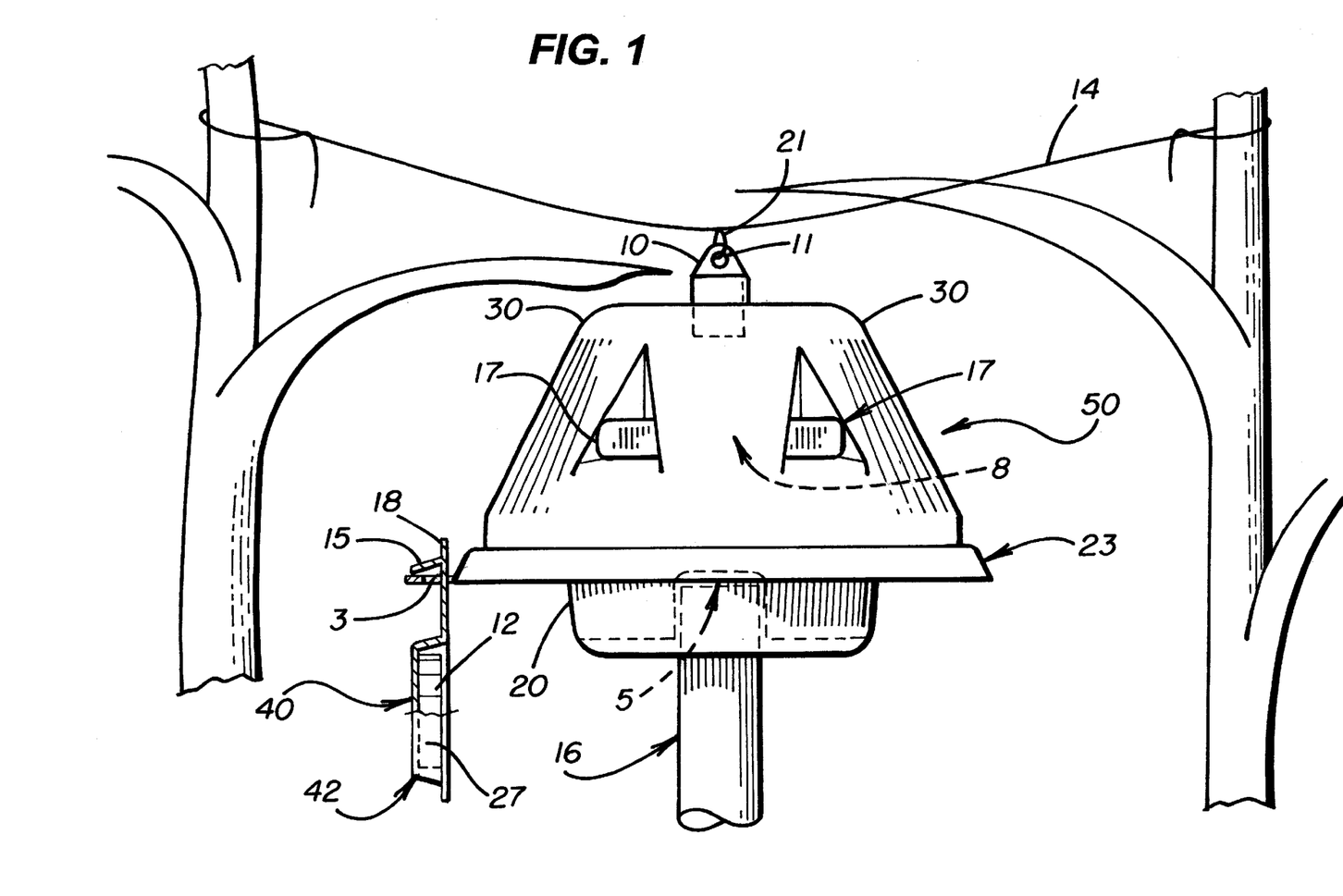
FIG. 1 is an external view of an assembled corn rootworm trap.
Figure 3:
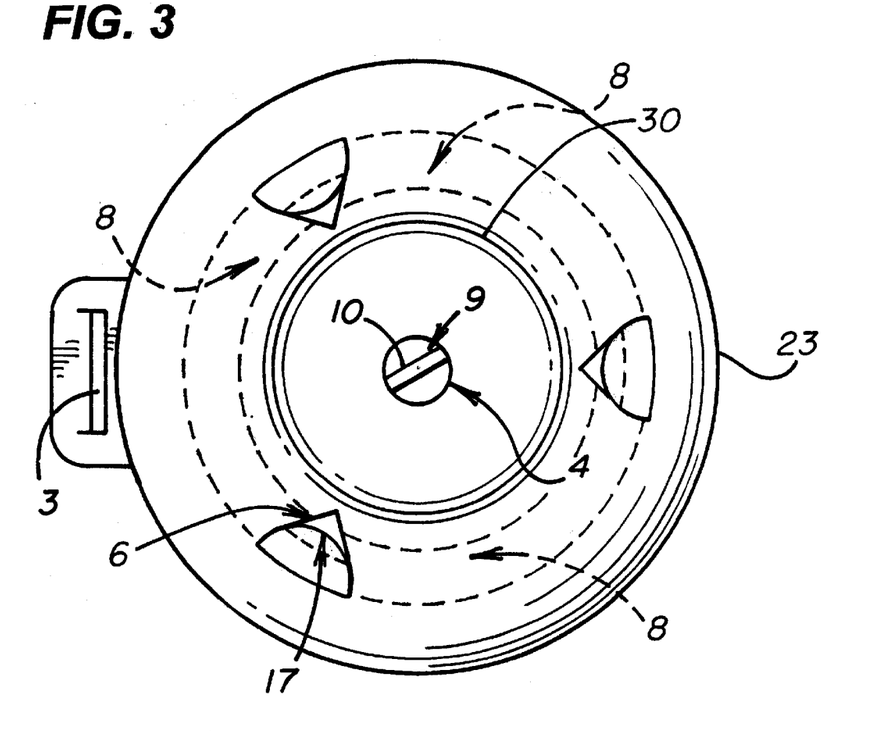
FIG. 3 is a top view of a trap capture top dome.

FIG. 1 shows an external side view of the trap of the invention. The assembled trap of the invention comprises four major components. The first component is a top dome 30 comprising the fourth component, namely a kill-bait 4 positioned within the kill-bait holder 9 placed in the center of the upper part of the top dome. The second component is an insect capture reservoir 20, which is a container serving as a receptacle for captured and killed insects. When the trap is assembled, the capture reservoir 20 is attached to the top dome 30 through a locking device 7 (shown in the inset) comprising top tabs 6, locking tabs 17 present on the top dome and a rim segments 24 present on the rim of the capture reservoir. Openings 8, formed by locking the locking tabs 17 to the rim segments 24, circumferentially interspace the locking tabs and permit insects' entry into the assembled trap 50. The rim segments 24 may further feature stops 25 (seen in FIG. 5) which permit the reservoir to be placed into the dome and rotated to lock it into place. The rim segments are optional but advantageous parts of the locking device. The stops 25 prevent the reservoir from being rotated past the location where the locking tabs 17 are engaged with the rim 19 or, preferably, with the rim segments 24. The capture reservoir 20 may be removed by rotating it in the opposite direction and lowering it out of the dome. The third component, namely a kairomone lure assembly 40, seen in detail in FIG. 3A, is inserted into a kairomone lure holder 42 which is attached externally to the top dome 30 through a female insertion slot 3. The lure holder 42 comprises a male insertion tab 18 with the lock 15 which, when inserted into a female insertion slot 3, locks the lure holder in place externally to the top dome, as seen in FIG. 1.

The trap is preferably made of a clear, transparent, flexible, light and durable plastic material, such as polyethylene (PET) or polyvinylchloride (PVC). The transparent material permits the user to see insects trapped inside and permits easy monitoring and handling of the trap without need to open the trap for inspection. However, the trap design and used material also permits easy emptying of the trap when it is full with captured insect. As stated above, the bottom portion of the trap, namely the capture reservoir snaps and locks easily into the upper portion, namely into the top dome and can be easily removed.

As seen in FIG. 1, the assembled trap 50 consists of a trap top dome 30 containing a kill-bait 4 placed within a kill-bait insertion slot 9 positioned in the upper center of the top dome. Also visible in the FIG. 1 are attachments means 10 and 11, which permit attachment of the trap to the tree or bush by hanging the trap on the metal or plastic wire 14. Top hanger insert hole 11 is particularly suitable for hanging a hanging wire, or, typically, plastic coated wire hanger, or any other hanging or attachment means. Attachment means top hanger 10 is a plastic protrusion molded to the central external portion of the top dome comprising opening or hole 11, through which the wire 14 may be conveniently inserted or which may contain a wire loop 21 for insertion of the hanging wire 14. Top hanger tab 10, comprising hole 11, is an integral piece of the trap's top dome. There is no opening from the inside of the trap to the outside of the trap. The hanging attachment means 10 is thus fully external. This is an important feature insuring that there is no interference in insect attraction from inside of the trap and that the insect is attracted solely to the outside of the entry area openings 8. Additionally, this feature assures also that the effect of the kill-bait feeding stimulant is not diluted from outside.

Plastic wire hanger 14 or other attachment means allow placement of trap between tall growing crops like corn or placing the trap in fields attached to the stakes 16 as seen in FIG. 1.

Figure 2:
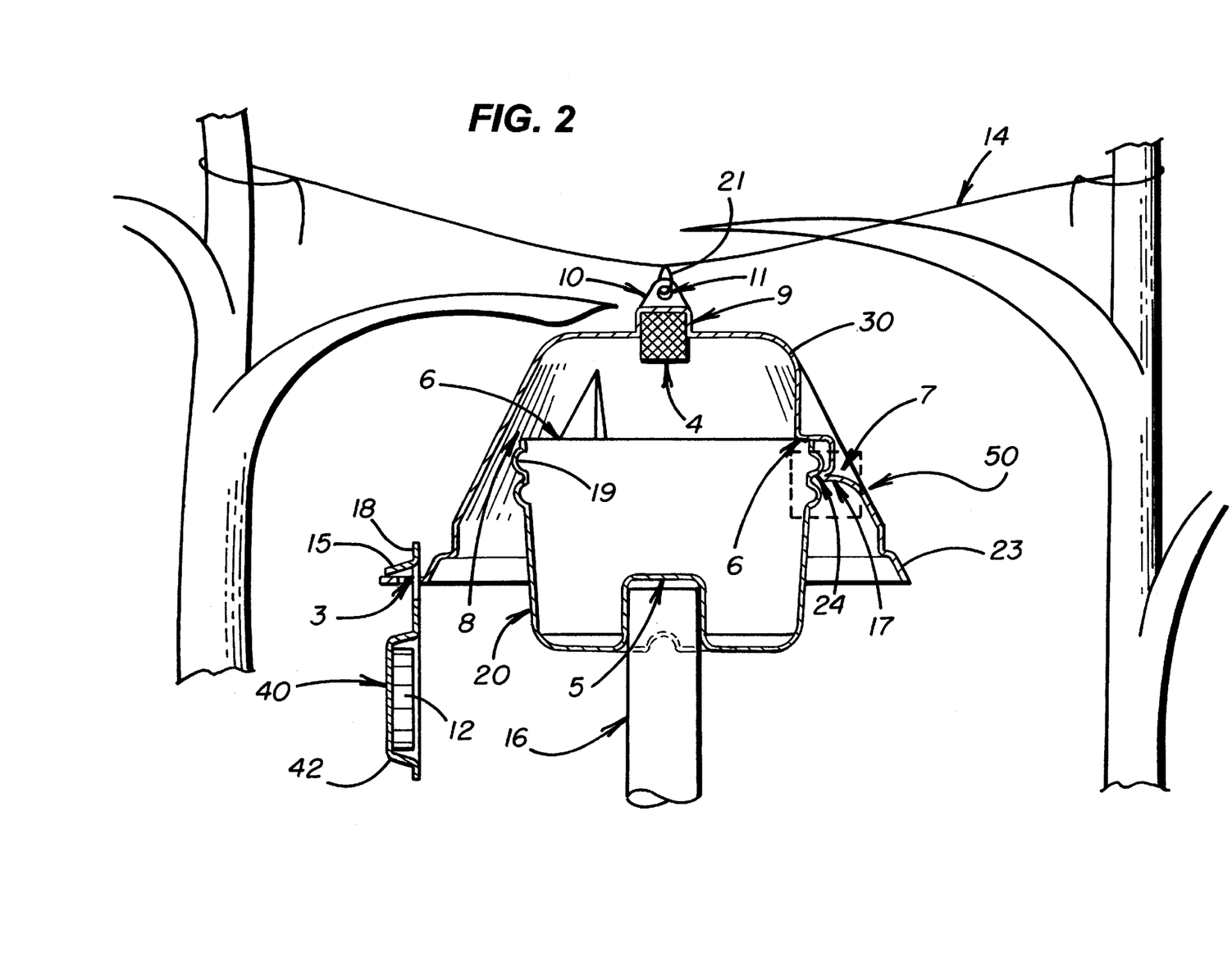
FIG. 2 is a section view of an assembled corn rootworm trap.

FIG. 2 is a cross-section view of the trap showing a placement of the capture reservoir 20 within the top dome 30, entryway openings 8, kill-bait holder 9 and kill-bait 4, the rim 19, locking device 7 (inset), the lure 40 and a socket 5.

Also seen in FIG. 2 is the locking device 7 (inset) comprising two or more locking tabs 17 and two or more stop tabs 6 optionally present on the inside of the top dome to permit easy positioning of the reservoir 20 within the top dome 30 and allowing the locking tabs to engage either with the rim 19 or rim segments 24. The locking tabs 17 lock into the rim 19 or into segments 24 of the capture reservoir. Openings 8 (also seen in FIG. 5) are formed by the space between two consecutive locking tabs engaged to the rim segments. FIG. 2 further shows rim components 24 of the capture reservoir 20 locked (snapped) into the top dome through the locking tabs 17. The locking tabs 17, in cooperation with the stop tabs 6 and with rim segments 24, control the size of the openings 8 and together with the rim 19 of the capture reservoir serve to lock the two pieces of the trap together as shown in FIG. 2.

Figure 5:
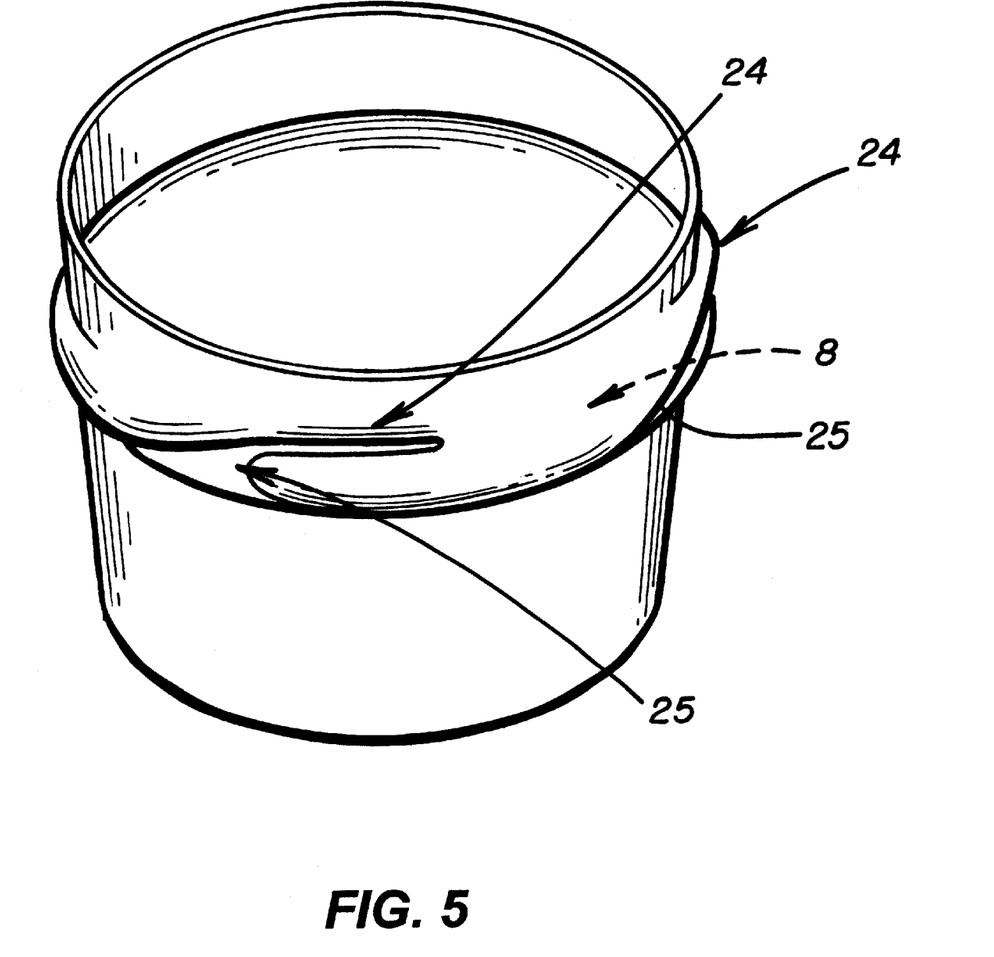
FIG. 5 is a side view of a trap capture reservoir illustrating placement of rim segments for engagement with locking tabs of the capture top dome.
Figure 6:
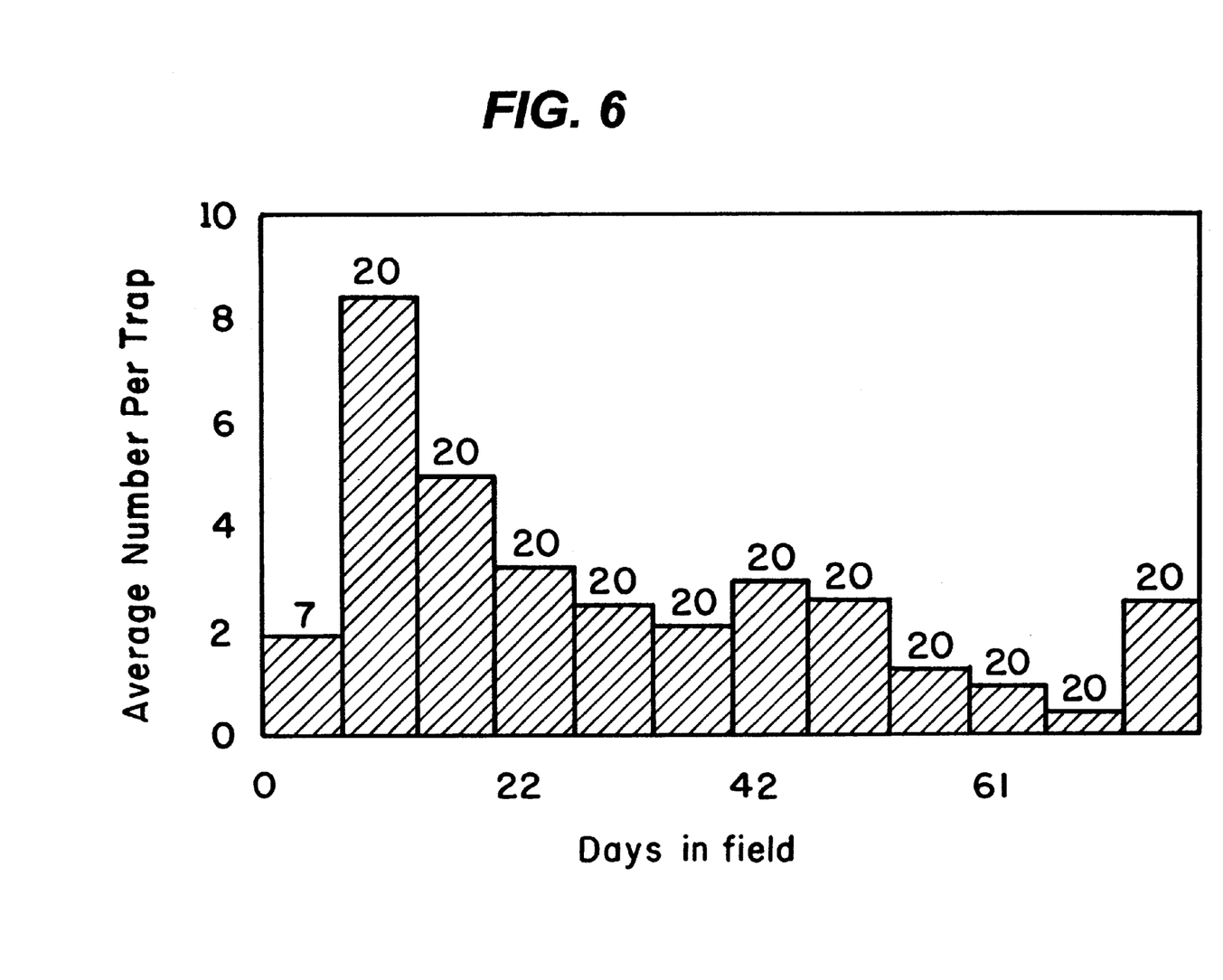
FIG. 6 shows results of trap capture of Southern corn rootworm during the season from July to September expressed as an average number per trap per week.

Stops 25, present on the rim segments, prevent closing and assure uniformity of the openings 8. This uniformity of the openings lowers variation in trap capture. Locking tabs 17 and rim segments are typically smooth in curvature with a depth of under ⅛ inch. Depths of locking tabs over this size severely reduce capture rate of the corn rootworm since the insect shows an aversion to crawling over the area and is, thus, not recommended, however, large or smaller size locking tabs may be suitable for capture of other insects.

Openings 8 between the trap top dome 30 and the capture reservoir 20 are uniform along the periphery of the trap and are essentially continuous around the periphery of the trap, except for the location of the locking tabs 17 engaged to the rim components, seen in FIG. 2 and FIG. 3. These openings permit the insect to enter the insect trap under the skirt 23 of the top dome 30 from any angle. Also continuous around the periphery is a rim 19 of the capture reservoir which is optionally interspaced with rim segments 24.

The trap capture reservoir 20 additionally and optionally contains a socket 5 allowing insertion of field stake 16. The presence of the socket 5 is optional but it is preferred as it provides the second means for attachment of the trap in the field. Socket 5 is particularly suitable for insertion of field stake 16, typically made from ⅜ inch PVC irrigation pipe. This attachment means is to be used as an alternative to the top hanging device for low growing crops.

The sides of both components of the trap, namely the top dome 30 and the capture receptacle 20 are angled and sloped to various degrees for maximum efficiency of trap entry by flying insect, particularly corn rootworm adults. However, the sides of the top dome or capture receptacle may also be straight or inverted, depending on the intended use. As discussed above, the bottom portion of the trap, the capture receptacle 20 easily snaps into the upper portion, that is, into the top dome 30 of the trap, and can be easily opened, removed, emptied or substituted for inspection or maintenance.

The third component shown herein attached externally to the top dome, namely kairomone lure assembly 40 is shown in detail in FIG. 4. Briefly, the assembly 40 comprises the kairomone lure 27 placed in the kairomone lure holder 42 and seal 12. The lure holder male tab 18 is inserted into female slot 3 positioned externally on the dome 20. Kairomone lure 27 is placed within the holder 42 and is covered with a laminated seal 12 which seals the kairomone lure 27 within the lure holder 42. The seal 12 consists of an inner layer of plastic, such as commercially available BAREX™ plastic, and an outer layer of foil. BAREX™ is preferably used as the seal for the kairomone lure 27 because it provides a necessary nonpermeable barrier extending the shelf-life of the lure and otherwise protecting the content of the lure from the environmental elements. In reverse, it also protects the user from the content of the lure.

Kairomone lure holder 42 further comprises a male insertion tab 18 which fits into female insertion slot 3 of the top dome. A lock-back tap 15 of the holder 42 prevents the tab 18 from falling out of female insertion slot 3 when the holder 42 is attached to the top dome. Kairomone lure assembly 40 is made of high void, highly absorbent polyethylene. The dispenser, therefore, absorbs a high rate of the active ingredients, releases them slowly and protects them from the environment.

Kill-bait 4 placed within the kill-bait holder 9 typically consists of a pill containing a mixture of the feeding stimuli with an insecticide bound together by a special, preferably paraffin formulation. Kill-bait insertion slot 9 is preferably tapered to insure a friction fit of the kill-bait pill.

FIG. 3 is a top view of the trap's top dome and shows locking tabs 17 as well as stop tabs 6 and openings 8. Also seen is the internally molded kill-bait holder 9 as a socket for insertion of the kill-bait 4. The female insertion slot 3 is attached externally on the side of the top dome for insertion of the male insertion tab 18 of the kairomone holder 42.

Figure 4A:
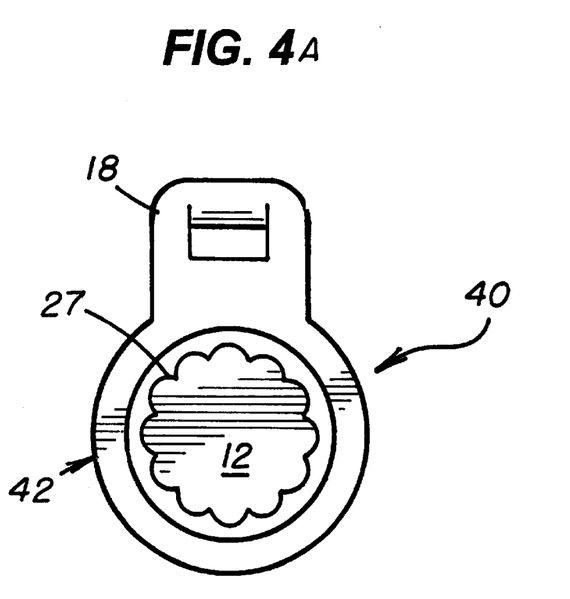
Figure 4B:
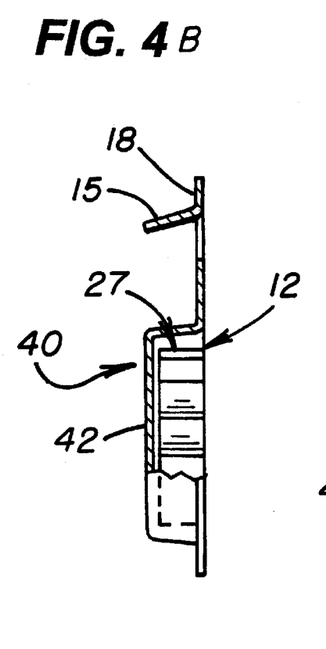

FIG. 4 shows a kairomone lure holder 42 in the front view (FIG. 4A) and in the side view (FIG. 4B). Kairomone lure container lock-back tab 15 is engaged when the lure holder tab 18 is inserted into the slot 3 and prevents the holder from falling out of the female insertion slot 3. As seen in FIG. 4, kairomone lure assembly 40 is a completely separate, stand alone component of the trap which can be easily added, removed or exchanged at will. The kairomone lure 27 is placed within the lure holder 42 and is typically circular in shape, although other shapes such as square, rectangular, triangle, star, etc., are also possible. The lure holder male insertion tab 18 extends from the holder and comprises a lock-back tab 15 which prevents unintentional disengagement of the lure holder from the trap. When the male insertion tab 18 is inserted into female slot 3 of the top dome, and the lock-back is engaged, the unintentional disengagement is virtually impossible without unlocking the lock-back tab 15.

FIG. 5 is a side view of a trap capture reservoir showing emplacement of rim segments 24 and stops 25 for engagement with the locking tabs 17 within the locking device 7. The trap capture reservoir 20 optionally can have segments 24 of a rim 19 shown in FIG. 5 optionally also comprising stops 25. The rim segments and stops are spaced to match the locking tabs 17. This allows the reservoir to be placed into the dome and rotated to lock it into place and assures uniformity of openings 8. The rim segments hold the trap in place exactly the same way a complete rim 19. The stops prevent the reservoir from being rotated past the location where the locking tabs 17 are engaged with the rim segments 24. The reservoir may be removed by rotating it in the opposite direction and lowering it out of the dome.

Although FIGS. 1 and 2 illustrate the preferred embodiment of the current invention, all variations of the trap in size, material used or shape are intended to be within the scope of the invention.

The trap of the invention has many new features which are advantageous for the trap's intended use. For example, the trap is made of light but durable plastic which is preferably transparent to allow the monitor to determine how many insects are captured and/or to empty or change the bottom capture reservoir. The bottom reservoir can be easily removed, emptied or exchanged and, thus when the trap becomes too full, it is easy to empty it without need for using the new trap or without removing the upper portion from the wire. This feature is important particularly for monitoring the number of insects and/or degree of infestation when the receptacle may be, for example, exchanged or checked on a daily, weekly or monthly basis to provide information on whether or not there is an infestation and the degree of the infestation. The primary function of the trap is, of course, a capture of and killing the insect but the detection and monitoring the degree of infestation leading to elimination of the infestation is equally important. The trap size, durable material and shape allows the use of the trap anywhere regardless of the environment or weather. It is made of completely non-toxic molded plastic material. There is no known insect which would eat and digest the used plastic material. The material is safe to be used even in instances where the trap is placed inside of the buildings, laboratory or green houses. Moreover, the plastic is reasonably hard so that it is break-proof and does not deteriorate or disintegrate in humid, dry, hot or cold weather.

Since the various specific kairomones and feeding stimuli may be selected, supplied and or used and exchanged for different insects, the current trap is very versatile, practical and economical and although it is described and was tested for the capture and monitoring of the corn rootworm, it is generally usable for any other insect. In such an instance, the corn rootworm kairomone and kill-bait is replaced with the appropriate alternatives.

The feeding stimuli may be any chemical compound or food which will attract the insect such as plant or oil-based food attractant, and it may be used alone or it may be a mixture of two or more compounds, for example, it may be a mixture of the food and insecticide. The mixture of both is then used to attract and kill the insect.

The new trap is more efficient in capturing both male and female insects than other existing traps over the full season because it uses the feeding stimulant effective to lure insect of both sexes and not the sex pheromone which only attracts males or females.

The kairomone lure, specific for corn rootworm, is selected from the group of compounds identified as 1,2,4-trimethoxybenzene, indole, trans-cinnamaldehyde, eugenol, 4-methoxyphenethanol and 4-methoxy cinnamaldehyde alone or in a mixture as seen in Table 1.

TABLE 1

CRW LURES

| Lure No. | Substrate | 1,2,4-Trimethoxybenzene | Indole | lure-Cinnamaldehyde | Eugenol | 4-Methoxy-phenthenol | 4-Methoxy Cinnamaldehyde |
|---|---|---|---|---|---|---|---|
| TRE 8274 | GP-202HV | 250 mg | 250 mg | 250 mg | | | 750 mg |
| TRE 8275 | GP-202 H.V. | | | | | | 1500 mg |
| TRE 8276 | GP-202 H.V. | 500 mg | 500 mg | 500 mg | | | |
| TRE 8279 | GP-202 H.V. | | | | 1500 mg | | |
| TRE 8280 | GP-202 H.V. | | | 1500 mg | | | |
| TRE 8281 | GP-202 H.V. | | | | | 1500 mg | |
| TRE 8282 | GP-202 H.V. | | | | | 750 mg | 750 mg |
| TRE 8291-1 | GP-202 H.V. | | 500 mg | 500 mg | 500 mg | | |
| TRE 8291-T | GP-202 H.V. | 500 mg | | 500 mg | 500 mg | | |
| TRE 8292 | GP-202 H.V. | 375 mg | 375 mg | 375 mg | 375 mg | | |
| TRE8326 | GP-202 H.V. | | | 750 mg | 750 mg | | |
| TRE 8331 | GP-202 H.V. | | | 750 mg | 750 mg | | |
| TRE 8336 | GP-202 H.V. | 500 mg | | 500 mg | | 500 mg | |
| TRE 8337 | GP-202 H.V. | | | | 750 mg | 375 mg | 375 mg |
| TRE 8336 | GP-202 H.V. | 250 mg | 250 mg | 250 mg | | | |
| TRE 8339 | ½ GP-202 H.V. | 500 mg | 500 mg | 500 mg | | | |
| TRE 8340 | ½ GP-202 H.V. | 250 mg | 250 mg | 250 mg | | | |
| TRE 8341 | GP-203 BRG-100 | 500 mg | 500 mg | 500 mg | | | |
| TRE 8342 | GP-203 BRG-100 | 250 mg | 250 mg | 250 mg | | | |
| TRE 8343 | FOAM | 500 mg | 500 mg | 500 mg | | | |
| TRE 8344 | FOAM | 250 mg | 250 mg | 250 mg | | | |
| TRE 8345 | ...POLY ROD | 500 mg | 500 mg | 500 mg | | | |
| TRE 8346 | POLY ROD | 250 mg | 250 mg | 250 mg | | | |

The effectivity of the CRW trap of the invention has been tested in various conditions and compared to the effectivity of the other types of traps. The results are described in Examples and shown in FIG. 4.

Utility

The insect trap of the invention has a novel design which is useful particularly for trapping and capturing the flying insect although, if properly positioned and if the proper kairomone or other attractant would be used, it would be equally useful for crawling insect and even larvae. The trap was developed, tested and proved very efficient, as evidenced by the following examples, for capturing corn rootworm and similar insects attacking a corn, peanut or leafy vegetable crop.

The trap design, herein called corn rootworm (CRW) trap, features attachments for two types of lures and baits. A kairomone based attractant provides full-season, long-range attraction for CRW adults to the trap. The adult corn rootworm is attracted to the trap and find its way into the top dome. As the corn rootworm enters the area inside the trap and under the dome skirt, it is lured to a full season feeding stimuli mixed with a small amount of insecticide toxicant (kill-bait) and, within a short time, is killed and falls into a capture reservoir forming a receptacle which can be removed for counting insects, cleaning the trap and replenishing or replacing baits, if and when necessary. The clear and durable plastic used for the trap allows multiple season use after replacement of lures and permits the user to see insects trapped inside.

The instant corn rootworm trap design thus features state of the art characteristics. The design considers insect behavioral preference, weather conditions, lure attractiveness, kill-bait effectiveness, multiple use, trap placement, efficiency of data collection and dead insect removal, ease of use and production cost.

The trap of the invention allows users to detect and monitor emergence and degree of infestation and accurately decide on treating corn rootworm populations based on the number and sex ratio of adults captured in the trap. The ability to accurately decide when the treatment is necessary compares favorably to current preventative treatments with insecticides applied to soil indiscriminately.

The instant trap is not only very efficient in capturing the insect but its monitoring capability leads to substantial reduction in the annual environmental pesticide load.

The following examples illustrate testing conditions and results of the trap testing against various insects.

EXAMPLE 1

Field Testing of the CRW Kairomone Trap
1. Corn Rootworm Trapping Studies

Corn rootworm trapping studies were conducted in summer. These field tests had three major objectives: (1) compare the timing and numbers of emerging Western and Mexican corn rootworm; (2) compare three types of traps for monitoring CRW emergence; and (3) compare two types of the CRW lures aged for different periods of time.

The field evaluations were conducted in five irrigated corn fields. Fields 1 and 2 were in the same county, fields 4 and 5 were in the same county but were in separate counties from each other as was the field 3.

For evaluation of the bait, only field 1 was used. Each bait type was placed down a row approximately 75 meters apart. The test was replicated five times with each replicate being 25 rows apart.

For evaluation for corn rootworm emergence, sticky traps, CRW traps baited with the 8276 lure, and emergence traps (modified pecan weevil traps) were used. The different types of traps were randomized approximately 75 meters down rows of corn. Each treatment was replicated five times, 25 rows apart, at each of the five test fields. The traps were deployed around July 1 and were serviced weekly except for the last period which lasted 11 days. At each sampling date, ten plants were sampled per replicate with a "Corn Kiss Sampler". This sampler used a leaf blower to blow a 180 mph airstream across the corn plant into a sampling net.

In the bait comparison, the CRW bait 8276 deployed for the length of the test, changed weekly, and aged ten days prior to the start of the test, were all about equal in the effectiveness against both the Western and Mexican corn rootworm (Tables 2 and 3). The most effective bait for both types of CRW was the bait 8337, changed weekly.

The results from these studies did not show a significant time difference in the emergence of Mexican and Western corn rootworm (Tables 2 and 3). The CRW population in the three county area was 90–95% Western corn rootworm and 5–10% Mexican corn rootworm. The emergence of both types of CRW was somewhat extended since capturing adults began the day the traps were deployed and continued until the traps were removed in August. Emerging adult CRW were captured over a 45-day period. The extended emergence may have been related to the cool, wet weather which prevailed at that time in the area.

TABLE 2

Numbers of Western Corn Rootworm Captured per Observation Period

| Field | Bait Tests | Day 1 | Day 8 | Day 15 | Day 22 | Day 29 | Day 96 | Total |
|---|---|---|---|---|---|---|---|---|
| 1 | Emergence Cage | 1.8 | 1.2 | 2.6 | 0.4 | 0.4 | 2 | 8.4 |
|  | Sticky Trap | 31.0 | 12.8 | 14.0 | 12.2 | 12.8 | 7.8 | 90.6 |
|  | Trece crw trap/8276 lure | 100.8 | 10.6 | 33.6 | 95.8 | 121.6 | 166.6 | 529 |
|  | Trece crw trap/lure 8276 aged 10 days | 62.4 | 16.2 | 42.2 | 129.8 | 179.8 | 151.4 | 581.8 |
|  | Trece crw trap/lure 8276 changed weekly | 74.4 | 18.6 | 42.2 | 142.8 | 206.6 | 175.8 | 660.4 |
|  | Trece crw trap/lure 8337 | 62.4 | 21.2 | 44.8 | 118.4 | 98.0 | 114.4 | 459.2 |
|  | Trece crw trap/lure 8337 changed weekly | 88.4 | 37.4 | 88.2 | 288.6 | 246.4 | 303.2 | 1052.2 |
|  | KISS # WCR/plant | 0.54 | 3.0 | 1.26 | 0.56 | 0.08 | 0.0 | 5.44 |
| 2 | Emergence Cage | 0 | 1.8 | 2.8 | 2.2 | 0.2 | 0 | 7 |
|  | Sticky Trap | 4 | 12 | 15.4 | 28 | 12.6 | 0.6 | 72.6 |
|  | Trece crw trap/8276 lure | 0 | 37.4 | 96.4 | 149.8 | 417.4 | 15.6 | 716.6 |
|  | KISS # WCR/plant | 0.26 | 1.48 | 1.1 | 1.04 | 0.04 | 0 | 3.92 |
| 3 | Emergence Cage | 0.8 | 0.6 | 0 | 0 | 0 | 0 | 1.4 |
|  | Sticky trap | 4.8 | 1.2 | 3.6 | 2 | 2.8 | 1 | 15.4 |
|  | Trece crw trap/8276 lure | 11.6 | 13.6 | 46.2 | 5.2 | 4.6 | 4.8 | 86 |
|  | KISS # WCR/plant | 0.26 | 1.46 | 0.12 | 0.22 | 0.2 | 0 | 2.26 |
| 4 | Emergence Cage | 3 | 5.6 | 0.4 | 0.2 | 0 | 0 | 9.2 |
|  | Sticky trap | 7.4 | 37 | 22 | 8.4 | 5.4 | 0.6 | 80.8 |
|  | Trece crw trap/8276 lure | 17.6 | 87.75 | 19 | 8.4 | 38 | 9.8 | 163 |
|  | KISS # WCR/plant | 0.1 | 0.82 | 0.26 | 0.08 | 0.08 | 0 | 1.34 |
| 5 | Emergence Cage | 1 | 3.2 | 4.2 | 2 | 0.2 | 0 | 10.6 |
|  | Sticky trap | 2.4 | 19.4 | 12 | 9.8 | 6.8 | 9 | 59.4 |
|  | Trece crw trap/8276 lure | 9.2 | 8.6 | 12.6 | 24.8 | 71 | 76.4 | 202.6 |
|  | KISS # WCR/plant | 0.26 | 2.24 | 0.52 | 0.68 | 0.34 | 0 | 4.04 |

Number of Captured Insects expressed as average number WCR per trap per observation period

TABLE 3

Numbers of Mexican Corn Rootworm Captured per Observation Period

| Field | Bait Tests | Day 1 | Day 8 | Day 15 | Day 22 | Day 29 | Day 36 | Total |
|---|---|---|---|---|---|---|---|---|
| 1 | Emergence Cage | 0.4 | 0 | 0.8 | 0 | 0.4 | 0.2 | 1.8 |
|  | Sticky trap | 1 | 0.2 | 1.4 | 1 | 0.5 | 0.2 | 4.4 |
|  | Trece crw trap/8276 lure | 3.4 | 1 | 3.4 | 4.4 | 4.2 | 5.4 | 21.8 |
|  | Trece crw trap/lure 8276 aged 10 days | 4.2 | 0.8 | 1.8 | 5.6 | 2.8 | 4.2 | 19.4 |
|  | Trece crw trap/lure 8276 changed weekly | 1.6 | 0.2 | 4 | 7.4 | 4.4 | 5 | 22.6 |
|  | Trece crw trap/lure 8337 | 6.6 | 0.6 | 4 | 4.2 | 3 | 3.8 | 22.2 |
|  | Trece crw trap/lure 8337 changed weekly | 3.4 | 0.4 | 22 | 10 | 6 | 9.4 | 36 |
|  | KISS # WCR/plant | 0 | 0.4 | 0.16 | 0 | 0.04 | 0 | 0.56 |
| 2 | Emergence Cage | 0 | 0.6 | 0.4 | 0 | 0.2 | 0 |  |
|  | Sticky trap | 0 | 0 | 0.2 | 1.8 | 0.2 | 0.4 | 2.6 |
|  | Trece crw trap/8276 lure | 0 | 7.4 | 6.8 | 3.8 | 5.8 | 0.6 | 24.4 |
|  | KISS # WCR/plant | 0 | 0.2 | 0.1 | 0.16 | 0 | 0 | 0.46 |
| 3 | Emergence cage | 0 | 0.2 | 0 | 0 | 0 | 0 | 0.2 |
|  | Sticky trap | 0 | 0.6 | 0 | 0.2 | 0 | 0 | 0.8 |
|  | Trece crw trap/8276 lure | 0.2 | 9 | 4.2 | 0.2 | 0.6 | 0.4 | 14.6 |
|  | KISS # WCR/plant | 0 | 0.26 | 0.04 | 0.06 | 0 | 0 | 0.36 |
| 4 | Emergence Cage | 1.2 | 0.8 | 0 | 0.2 | 0 | 0 | 2.2 |
|  | Sticky trap | 1.8 | 7.6 | 1.8 | 1 | 0.2 | 0.2 | 12.6 |
|  | Trece crw trap/8276 lure | 1.6 | 12.25 | 0.6 | 1 | 1.4 | 0.6 | 15 |
|  | KISS # WCR/plant | 0 | 0.34 | 0.06 | 0.06 | 0.02 | 0 | 0.48 |
| 5 | Emergence Cage | 1.4 | 0.4 | 1.4 | 0.8 | 0 | 0 | 4 |
|  | Sticky trap | 0.4 | 2 | 0.2 | 0.2 | 0.4 | 0.4 | 3.6 |
|  | Trece crw trap/8276 lure | 2.4 | 4 | 2.6 | 1.4 | 3.4 | 3.6 | 17.4 |
|  | KISS # WCR/plant | 0 | 0.14 | 0.12 | 0.1 | 0.04 | 0 | 0.4 |

Number of captured insects expressed as average number MCR per trap

2. Lure and Trap Comparison

The research results for the lure and trap comparison tests for both the Western (w) and Southern (s) corn rootworms. These tests were conducted at the Rootworm Area wide Project's "treated" area. However this field did not reach the treatment threshold. The corn rootworm populations, both species, were adequate to discern differences.

A. Lure Test for Western Corn Rootworm

In order to compare various lure formulations of corn rootworm (CRW) kairomone for optimum results against Western and Southern CRW, the field finals were run by the Kansas State University. The trials compared various sticky and non-sticky kairomone based trap designs for efficacy.

Four replicates of eleven different formulations were tested and changed at four week intervals. Traps were observed, counted and emptied at seven day intervals, data recorded and entered. Traps were placed at a density of 60 feet of row. Kill-bait was changed only when necessary.

Various trap designs and/or refinements were tested using sticky traps or kairomone type traps. Non-baited dull sticky traps were replicated four times. Kairomone lures were changed twice per season. Traps were observed and counted at seven day intervals.

3. Southern Corn Rootworm Trapping Program

The field testing of trap catching was performed. Results are seen in FIG. 4. FIG. 4 illustrates Southern corn rootworm trapping from July to September. As seen in FIG. 4, three adult insect peaks were observed during the tested season, which corresponded well with measured larval activity observed afterwards in the peanuts fields.

4. Lure Comparison for Western and Northern Corn Rootworm

This study compares nine different trap designs. Another study compares twelve different lure formulations. Lures were changed weekly and seasonally. The number of captures Western and Northern corn rootworm adults were calculated per trap per testing period. Pherocon AM and Trece traps are the proprietary traps of the Trece Corporation. Sutter, Multigard and Concept traps are commercially available from.

Trap 1=Trece clear top and bottom trap
Trap 2=Trece clear top and white bottom trap
Trap 3=Trece clear top and yellow bottom trap
Trap 4=Sutter trap
Trap 5=Concept trap
Trap 6=Pherocon AM with lure
Trap 7=Multigard with lure
Trap 8=Pherocon AM without lure
Trap 9=Multigard without lute There was no statistical difference between various Trece designs, Sutter and Concept (modified boll weevil trap) kairomone trap designs. Multigard sticky traps with kairomone lure were more attractive than other designs. But, Trece non-sticky designs demonstrated excellent efficiency for seasonal monitoring of CRW.

Lures most attractive to Western and Northern CRW appeared to be attractive full season.

What is claimed:

1. An insect trap comprising:
   a) a capture top dome with an externally attached removable kairomone lure holder;
   b) a removable capture reservoir comprising a circular rim for locking the top dome to the capture reservoir;
   c) insect entry openings;
   d) a kairomone lure wherein said lure is a kairomone-based attractant selected from the group consisting of 1, 2, 4-trimethoxybenzene, indole, transcinnamaldehyde, eugenol, 4-methoxyphenethanol, 4-methoxycinnamaldehyde, and a combination thereof;
   e) a removable kairomone lure dispenser comprising the kairomone lure sealed within a kairomone lure holder with a seal consisting of an inner layer of plastic and an outer layer of foil;
   e) a kill-bait pill placed into a kill-bait holder indent positioned in the upper center of the top dome wherein the kill-bait is a pill comprising a mixture of a feeding stimulant and an insecticide;
   f) a locking device comprising two or more locking tabs circumferentially interspaced with the insect entry openings, two or more stop tabs positioned on the top dome preventing closing of said openings wherein during the trap assembling the locking device locks the top dome into the rim of the capture reservoir; and
   g) attachment means comprising either a top hanger positioned externally on the top of the top dome for attaching the assembled trap externally or a socket indented in a center bottom portion of the capture reservoir for insertion of a field stake into said socket, or comprising both the top hanger and the socket indented in the bottom capture reservoir permitting the attachment of the trap to tall growing crops and insertion of the field stake for low growing crops.

2. The trap of claim 1 wherein the feeding stimulant is cucurbitacin and insecticide is carbaryl.

3. The trap of claim 2 wherein the cucurbitacin and carbaryl are formulated in about 60% paraffin of a melting point above 160° F.

4. The trap of claim 1 wherein the locking tabs in cooperation with the stop tabs control the size of the insect entry openings.

5. The trap of claim 1 wherein the kairomone lure holder is inserted into a female insertion slot positioned on an exterior surface of the top dome.

6. The trap of claim 1 wherein the capture reservoir is attached to the top dome by locking the locking tabs and is removed by unlocking the locking tabs.

7. The trap of claim 1 wherein the locking tabs are engaged with a rim segment of the capture receptacle.

8. The trap of claim 7 wherein the locking device comprises two or more locking tabs evenly circumferentially spaced within a down sloping wall of the top dome facing inwards and wherein a circumferential rim of the capture reservoir is interspaced with rim segments spaced to match the locking tabs.

9. A multi-part insect trap assembly for assembling into an insect trap for capture of flying or crawling insect, said assembly comprising:
   a) a capture top dome for attachment to an insect capture reservoir comprising a kill-bait and a kairomone lure dispenser;
   b) the insect capture reservoir;
   c) the kairomone lure dispenser;
   d) the kill-bait;
   e) a locking device for locking the capture top dome onto said capture reservoir; and
   f) attachment means positioned on a top of the capture top dome and in a bottom center of the capture reservoir;
   wherein, after assembling said insect trap, the locking device locks the capture top dome and the capture reservoir together in a position forming openings for insect entry, wherein said locking device locks the top dome into a circular rim positioned on the capture reservoir, said locking device further comprising two or more locking tabs and two or more stop tabs positioned on the top dome;

wherein said locking tabs are circumferentially interspaced with said openings for insect entry and wherein the stop tabs prevent closing of said openings;

wherein said kill-bait is a pill placed into a kill-bait holder indent positioned in an upper center of the top dome;

wherein said kairomone lure dispenser comprises a kairomone lure holder wherein said kairomone lure holder is externally attached to the top dome;

wherein the feeding stimulant is cucurbitacin and the insecticide is carbaryl; and wherein the attachment means is a top hanger for hanging the assembled trap, said top hanger positioned externally on the top of the top dome, and a socket for insertion of a field stake, said socket indented in a center bottom portion of the capture reservoir.

10. The assembly of claim 9 wherein the openings between the top dome and the capture reservoir allow the insects to enter the trap from any direction.

11. A method for capturing, killing or monitoring insects, said method comprising steps:

a) assembling an insect trap for capture of flying insect by attaching a capture top dome forming an upper portion of the trap to a removable capture reservoir forming a lower portion of the trap, wherein the capture top dome and the capture reservoir are attached by means of a locking device comprising two or more circumferentially spaced locking tabs and two or more circumferentially spaced stop tabs, said locking tabs removably attached to a rim of the capture reservoir and forming insect entry openings;

wherein the capture top dome comprises in its upper center a kill-bait insertion slot for insertion of a kill-bait pill and externally placed slot for attaching a kairomone holder;

b) inserting a kill-bait into the kill-bait insertion slot;

c) attaching the kairomone holder to the externally placed holder wherein said kairomone holder comprises a kairomone attractant;

d) attracting an insect into the capture reservoir through the insect entry openings by means of the kairomone attractant; and e) counting a number of captured and killed insect collected within the capture reservoir and expressing the number of captured and killed insect per a selected period of time.

* * * * *